US00PP08090P

United States Patent [19]

Walters, deceased

[11] Patent Number: Plant 8,090

[45] Date of Patent: Jan. 5, 1993

[54] VARIETY OF GERANIUM NAMED PRINCE

[75] Inventor: Ernest Walters, deceased, late of Nottingham, Great Britain, by Mary Bodill, administrator

[73] Assignee: Oglevee, Ltd., Connellsville, Pa.

[21] Appl. No.: 699,464

[22] Filed: May 13, 1991

[51] Int. Cl.[5] ..... A01H 5/00

[52] U.S. Cl. ..... Plt./87.12

[58] Field of Search ..... Plt./68, 87.12

[56] References Cited

U.S. PATENT DOCUMENTS

P.P. 6,020 9/1987 Kirmann ..... Plt. 87.12

*Primary Examiner*—Howard J. Locker

*Attorney, Agent, or Firm*—Webb, Burden, Ziesenheim et al.

[57] ABSTRACT

This variety is characterized by a wiry plant habit which withstands abuse without damage. Its full flower head is slow to form and slow to shatter extending the shelf life. The variety roots easily, has free basal branching. Its compact, neat growth habit offers a unique flower form and presentation. The medium purple flower with a rich burgundy blotch contrasts nicely with the deep green foliage.

1 Drawing Sheet

BACKGROUND OF THE INVENTION

The present invention comprises a new and distinct cultivar of *Pelargonium*×*domesticum* known by the varietal name Prince (Oglevee No. 413; Walters No. 21W-0). The new variety was discovered by Mr. Ernest Walters in a selected breeding program in Hucknall, Nottingham, Great Britain. The new variety is a selection from the crossing of *P. crispum*×Prince William. The new variety was first asexually reproduced in the United States by cuttings at Oglevee, Ltd., in Connellsville, Pa. in January of 1987. The new variety has been asexually reproduced by cuttings at Oglevee, Ltd. in Connellsville, Pa. over a several years period. It has also been trialed at Connellsville and has been found to retain its distinctive characteristics through successive propagations.

The cultivar when grown in a glass greenhouse in Connellsville, Pa. using natural light and 60° F. night and 68° F. day, has a response time of 14 weeks from a rooted cutting to flowering in a 6 inch pot. The response time was determined to plants grown in soilless media employing constant fertilizer 150–200 parts per million of nitrogen and potassium in full light. The rooted cuttings were potted on Nov. 1, 1989 and flowered on Feb. 15, 1990.

DESCRIPTION OF THE DRAWING

The accompanying photographic drawing illustrates the new cultivar, with the colors shown being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on fourteen-week plants blossomed under natural light in a greenhouse and the color readings were taken indoors under 200–220 foot candles of florescent cool white light. Color references are primarily to the R.H.S. Colour Chart of The Royal Horticultural Society of London.

THE PLANT

Classification:

*Botanical.*—*Pelargonium*×*domesticum.*

*Commercial.*—Regal Geranium.

Form: Compact mound.

*Height.*—29.5 cm from media surface.

*Growth.*—Strong, wiry.

Foliage: Stalked leaf attachment.

Leaves:

*Size.*—7.3 cm to 8.0 cm across.

*Shape.*—Depressed ovate. Base: cuneate to truncate to reniform.

*Margin.*—Serrately lobed.

*Texture.*—Leathery; slightly hairy.

*Color.*—Top: Green Group 137B. Bottom: Yellow/Green Group 146B.

*Ribs and veins.*—Palmate veination. Color: Yellow/Green Group 147C.

Petioles:

*Length.*—5.2 cm to 5.5 cm.

Stem:

*Color.*—Yellow/Green Group 146B.

*Internodes.*—1.0 cm to 1.5 cm in length.

THE BUD

Shape: Elliptical.

Size: 1.5 cm to 1.7 cm in length (tight bud no color showing).

INFLORESCENCE

Blooming habit: Continuous; many medium-sized florets; slow to shatter.

Size: 6.5 cm to 7.5 cm across.

Borne: Umbel; floret on pedicel, pedicel on peduncle.

Florets:

*Form.*—Cupped.

*Color.*—Top: Red/Purple Group 72B with a dark blotch on all five petals. Center: Blotch—Greyed/Purple Group 187A; dark veining extends from blotch into outer margin. Bottom: Red/Purple Group 73D; Blotch-Greyed/Purple Group 187A.

*Petals.*—Separate, not united; margin entire; 5 in number.

*Size.*—3.5 cm to 4.0 cm across.

*Texture and appearance.*—Satiny; appearance from a distance is a medium purple flower with a rich burgundy blotch on all five flower petals atop a foliage canopy of deep green.

Petaloids: None present.

Pedicel:

*Length.*—1.5 cm to 2.0 cm.

*Color.*—Yellow/Green Group 146C.

Peduncle: 7.0 cm to 8.0 cm in length.

*Color.*—Yellow/Green Group 146B.

Disease resistance: Not known.

Lasting quality: Full flower head is slow to form, extending the shelf life; slow to shatter; wiry plant habit can withstand more abuse without damage.

REPRODUCTIVE ORGANS

Stamens:

*Anthers.*—1 mm to 2 mm in length.

*Filaments.*—White, 5 mm to 9 mm in length.

*Pollen.*—None present.

Pistils:

*Number.*—One.

*Length.*—1.0 cm to 1.5 cm.

*Stigma.*—5 to 6 parted. Color: Red/Purple Group 59B.

*Style.*—0.5 cm to 1.0 cm in length. Color: Red/Purple Group 59B.

Ovaries: Superior; pale green, pubescent; 4.0 mm to 5.0 mm in length.

Fruit: None observed.

GENERAL CHARACTERISTICS

This new variety of *Pelargonium*×*domesticum* is an improvement over the current Regal varieties on the market today. Ease of rooting; free basal branching; compact, neat habit along with a unique flower form and presentation make this variety a welcome addition to current production. The medium purple flower with a rich burgundy blotch contrasts nicely with the deep green foliage.

It is claimed:

1. A new and distinct variety of Geranium plant substantially as shown and described.

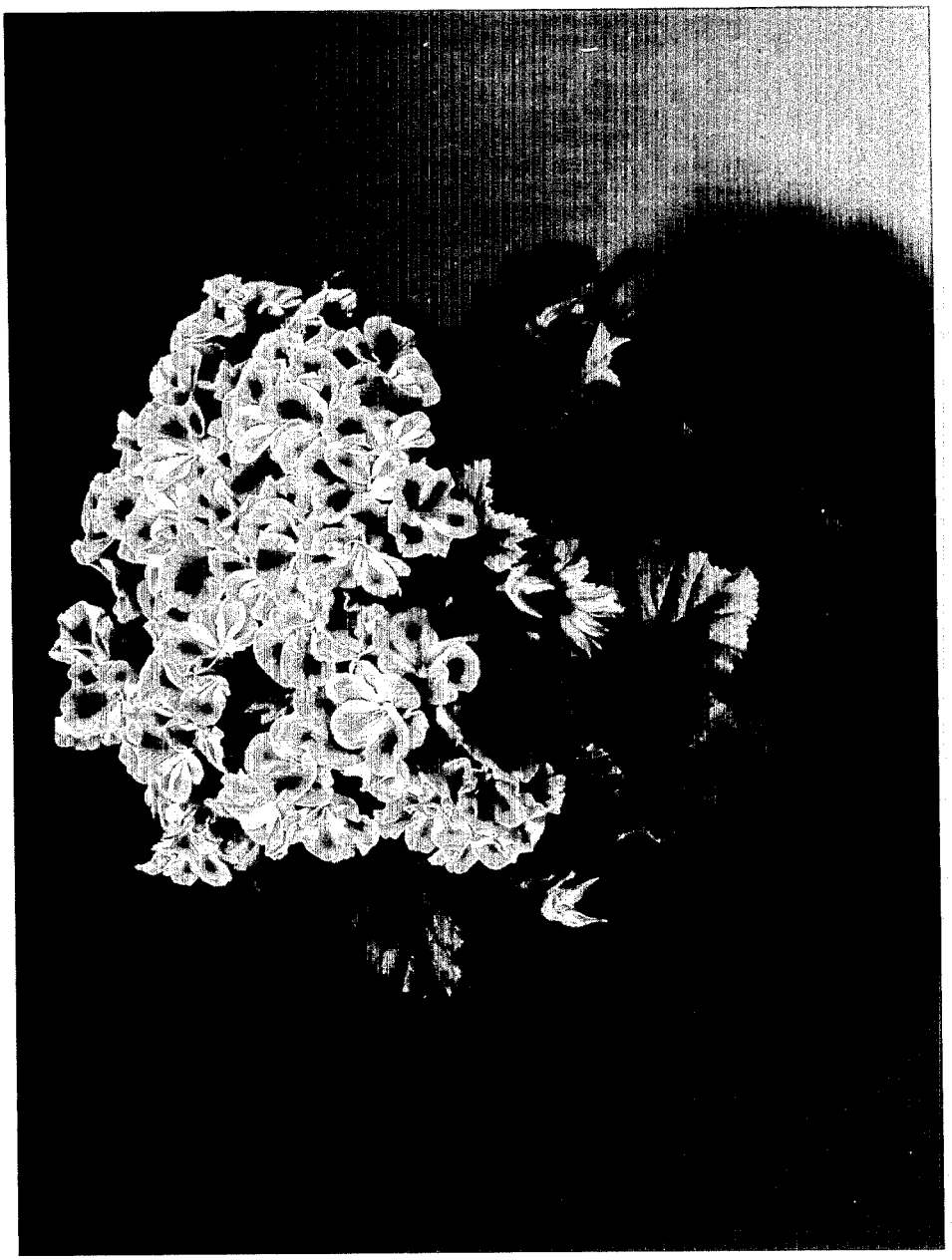

* * * * *